United States Patent [19]

Uddin

[11] Patent Number: 5,187,092
[45] Date of Patent: Feb. 16, 1993

[54] SOMATIC EMBRYOGENESIS IN GYMNOSPERMS

[75] Inventor: M. Rafique Uddin, Atlanta, Ga.

[73] Assignee: Institute of Paper Science and Technology, Inc., Atlanta, Ga.

[21] Appl. No.: 497,445

[22] Filed: Mar. 22, 1990

[51] Int. Cl.$^5$ .............................................. C12N 5/00
[52] U.S. Cl. ........................ 435/240.45; 435/240.49; 435/240.54
[58] Field of Search ...................... 435/240.45, 240.49, 435/240.54

[56] References Cited

U.S. PATENT DOCUMENTS

| | | | |
|---|---|---|---|
| 3,979,198 | 9/1976 | Bardsley | 71/1 |
| 4,199,897 | 4/1980 | Greenwood | 47/58 |
| 4,217,730 | 8/1980 | Abo El Nil | 47/58 |
| 4,354,327 | 10/1982 | Smeltzer et al. | 47/58 |
| 4,377,921 | 3/1983 | Mehra-Palta et al. | 47/58 |
| 4,417,417 | 11/1983 | Mehra-Palta | 47/58 |
| 4,612,725 | 9/1986 | Driver | 47/58 |
| 4,771,002 | 9/1988 | Gelvin | 435/172.3 |
| 4,801,545 | 1/1989 | Stuart et al. | 435/240.45 |
| 4,957,866 | 9/1990 | Gupta et al. | 435/240.4 |
| 5,034,326 | 7/1991 | Pullman et al. | 435/240.4 |
| 5,036,007 | 7/1991 | Gupta et al. | 435/240.45 |
| 5,041,382 | 8/1991 | Gupta et al. | 435/240.45 |

OTHER PUBLICATIONS

Boulay et al. 1988. Plant Cell Reports 7:134-137.
Konar, R. 1974. Physiol. Plant. 32:193-197.
Gupta et al. 1987. Bio/Technology 5(7):710-712.
von Arnold et al. 1986. J. Plant Physiol. 122:261-265.
Brown et al. 1977. TAPPI J 60(6):72-73.
Bonga, J. 1980. In Vitro 16(3):233.
Hakman et al. 1988. Physiol. Plant. 72:579-587.
Nagmani et al. 1991. 21st Southern Forest Tree Improvement Conf., Knoxville, Tenn., Jun. 17-20, 1991.
Becwar et al., *Plant Cell Rep.*, vol. 6, pp. 35-38 (1987).
Durzan and Gupta, *Plant Science*, vol. 52, pp. 229-235 (1987).
Gupta and Durzan, *Plant Cell Rep.*, vol. 4, pp. 177-179 (1985).
Gupta and Durzan, *Biotechnology*, vol. 5, pp. 147-151 (1987).
Murashige and Skoog, *Physiol. Plant.*, vol. 115, pp. 473-497 (1962).
Shenk et al., *Can. J. Bot.*, vol. 50, pp. 199-214 (1972).
Verhagen et al., *Plant Cell, Tissue and Organ Cult.*, vol. 16, pp. 103-111 (1989).
White, Philip R., *The Cultivation of Animal and Plant Cells*, 2nd ed., The Ronald Press Co. (New York 1963).
Becwar et al., "Initiation of Embryogenic Cultures and Somatic Embryo Development in Loblolly Pine (*Pinus taeda*)", *Can. J. For. Res.*, vol. 20, pp. 810-817 (1990).
Bucholz et al., "Development of Seeds and Embryos in *Pinus ponderosa*, With Special Reference To Seed Size", *Illinois Acad. Sci. Trans.*, vol. 38, pp. 27-50 (1945).
Huang et al., "Plant Tissue Culture Media", *TCA Manual*, vol. 3, pp. 539-548, Tissue Culture Assoc. (Rockville, Md. 1977).
Becwar et al., "Development and Characterization of In Vitro Embryogenic Systems in Conifers", in *Somatic Cell Genetics of Woody Plants*, ed. Ahuja, M. R., Kluwer Academic Publishing, Dordrecht, The Netherlands (1988) pp. 1-18.

*Primary Examiner*—David T. Fox
*Attorney, Agent, or Firm*—Woodcock Washburn Kurtz Mackiewicz & Norris

[57] ABSTRACT

The invention is directed to the successful generation of mature embryos from gymnosperm somatic tissue using various combinations and proportions of glucose, maltose, abscisic acid and/or indolebutyric acid.

38 Claims, No Drawings

SOMATIC EMBRYOGENESIS IN GYMNOSPERMS

BACKGROUND OF THE INVENTION

Somatic embryogenesis is one of a number of methods known in the art for the propagation of desireable species or varieties of plants. There are many advantages, however, which favor somatic embryogenesis as a propagative method of choice. One advantage is that a plant which has a known and desirable phenotype can be chosen as the source of cells, and, in accordance with somatic embryogenesis techniques, these cells can be rapidly cultured into many genetically uniform embryos. The resulting embryos can then be cultivated into entire plants possessing roots and shoots. Thus, in accordance with this technique, plants with the same desirable phenotype as the parent can be mass produced, potentially at costs comparable to and often more quickly and with better genetic uniformity than other propagative techniques such as, for example, the generation of field grown seed.

The process of producing embryos from somatic tissues, however, requires the development of an embryogenic culturing medium and protocol suitable for the particular type of tissue. Various media and procedures have been attempted, but only some have been met with success.

Stuart et al., U.S. Pat. No. 4,801,545, for example, describes a medium for culturing somatic plant cells comprising 7.5 to 300 mM maltose along With a balanced salt solution containing plant cell nutritional and growth requirements. Also disclosed and claimed is a method of producing embryonic tissue from somatic tissue, specifically leguminosae somatic tissue, wherein the somatic tissue is regenerated to form embryonic tissue in a growth medium containing 7.5 to 300 mM maltose and at least one amino acid selected from the group consisting of proline, alanine and glutamine in an amount sufficient to stimulate somatic embryogenesis or embryo conversion.

Promoting successful somatic embryogenesis with woody species of plants, such as the gymnosperms, has been much more difficult than with foliage plants. However, researchers have achieved some success in this area also.

Abo El-Nil, U.S. Pat. No. 4,217,730, for example, describes methods for generating embryoids and plantlets from gymnosperm plant tissue through the use of tissue culture techniques. In one embodiment, the method comprises culturing excised gymnosperm plant tissue on a medium containing mineral nutrients, organic nutrients and auxins (as the sole exogenous plant hormone) until a soft callus tissue has developed, transferring the callus tissue into a suspension medium containing similar nutrients and hormone components (again, wherein auxins are the sole exogenous plant hormone), and agitating the suspension gently to produce embryoids. In another embodiment, the disclosed method comprises culturing excised gymnosperm plant tissue on a first medium containing mineral salts, organic nutrients, and an auxin selected from the group consisting of 2-4-dichlorophenoxyacetic acid and naphthalene-2-acetic acid until the formation of a soft callus, transferring the callus tissue into a suspension medium in which the callus is gently agitated, the suspension medium being similar in nutrient and hormone components to the first medium, and removing the resultant embryoids and placing them on a solid growth medium. MS basal medium, employed therein, includes various inorganic salts, as well as organic compounds, such as 3-indoleacetic acid, kinetin and sucrose, as set forth in Murashige and Skoog, *Physiol. Plant.* Vol. 115, pp. 473-497, at 475 (1962) (cited therein).

Gupta and Durzan, *Biotechnology*, Vol. 5, pp. 147-151 (1987), describes the somatic polyembryogenesis of the loblolly pine (*Pinus taeda* L.) using multiple phase culturing methodology employing MS basal medium variously supplemented with such compounds as 2,4-dichlorophenoxyacetic acid, kinetin, benzyladenine and sucrose. MS basal medium, as contemplated therein, includes various inorganic salts, as well as organic compounds, such as 3-indoleacetic acid, kinetin and sucrose, as noted in Gupta and Durzan, *Biotechnology*, Vol. 5, pp. 147-151, at 150-151 (1987), and Murashige and Skoog, *Physiol. Plant.* Vol. 115, pp. 473-497, at 475 (1962) (cited therein).

Durzan and Gupta, *Plant Sciences.* Vol. 52, pp. 229-235 (1987), describes the somatic embryogenesis and polyembryogenesis in Douglas-fir (*Pseudotsuga menzesii*) cell suspension cultures using multi-step culturing techniques employing MS basal medium and DCR basal medium variously supplemented with such compounds as 2-4-dichlorophenoxyacetic acid, kinetin, N-benzylaminopurine, abscisic acid and sucrose. DCR basal medium, as contemplated therein, includes various inorganic salts, as well as organic compounds such as sucrose, as set forth in Gupta and Durzan, *Plant Cell Rep.*, Vol. 4, pp. 177-179, at 177 (1985) (cited therein).

Mehra-Palta, U.S. Pat. No. 4,417,417, discloses methods of clonal propagation of gymnosperms in which excised gymnosperms tissue is treated on a nutrient medium containing cytokinin for a time sufficient to induce formation of adventitious buds. If desired, an auxin, such as indole-3-butyric acid, may be included in this step. The bud containing tissue is then transferred to a nutrient medium free of exogenous growth factors and maintained thereon until the induced adventitious buds produce rootable shoots. The rootable shoots may then be rooted using conventional techniques, but are preferably treated on a nutrient medium containing an auxin, such as indole-3-butyric acid, for a time sufficient to induce formation of adventitious roots, and are then transferred to a nutrient medium free of exogenous growth factors until the shoots are rooted. Suitable nutrient medium includes various inorganic salts, as well as organic compounds, such as sucrose.

Despite some success in developing suitable culture media and culturing processes for somatic embryogenesis, new and/or better media and methods, particularly for the commercially significant gymnosperm forest trees, are needed. The present invention is directed to this important end.

SUMMARY OF THE INVENTION

The present invention is directed to the successful production of mature embryos from gymnosperm somatic tissues. Specifically, the invention pertains to a method of producing mature embryonic tissue from gymnosperm somatic tissue comprising culturing said somatic tissue in a medium containing at least about 3% of a sugar selected from the group consisting of glucose and maltose and at least about 10 μM abscisic acid. As an alternative method, mature embryonic tissue is produced by culturing gymnosperm somatic tissue in a medium containing at least about 3% of a sugar selected from the group consisting of glucose and maltose and at least about 10 µM abscisic acid, and then in a medium containing at least about 3% maltose, at least about 20 µM abscisic acid and, optionally, at least about 0.1 µM indolebutyric acid.

The present invention is also directed to a medium for the production of mature embryonic tissue from gymnosperm somatic tissue. Specifically, the invention is directed to an embryogenic medium for the production of mature embryonic tissue comprising a culture medium containing at least about 3% of a sugar selected from a group consisting of glucose and maltose and at least about 10 µM abscisic acid. The invention also contemplates an embryogenic medium for the production of mature embryos comprising, in combination, (i) a culture medium containing at least about 3% of a sugar selected from the group consisting of glucose and maltose and at least about 10 µM abscisic acid, and (ii) a culture medium containing at least about 3% maltose, at least about 20 µM abscisic acid and, optionally, at least about 0.1 µM indolebutyric acid.

DETAILED DESCRIPTION OF THE INVENTION

The present invention is generally applicable to somatic tissue obtained from gymnosperms, the so-called soft woods which comprise the great bulk of the commercially important species utilized by the lumber industry. Among the more important of the gymnosperms are the pines which include the loblolly pine (*Pinus taeda*), slash pine (*Pinus elliotti*), sand pine (*Pinus clausa*), longleaf pine (*Pinus palustrus*), Monterey pine (*Pinus radiata*), shortleaf pine (*Pinus echinata*), ponderosa pine (*Pinus ponderosa*), Jeffrey pine (*Pinus jeffreyi*), red pine (*Pinus resinosa*), pitch pine (*Pinus rigida*), jack pine (*Pinus banksiana*), pond pine (*Pinus serotina*), Eastern white pine (*Pinus strobus*), Western white pine (*Pinus monticola*), sugar pine (*Pinus lambertiana*), Virginia pine (*Pinus virginiana*), and lodgepole pine (*Pinus contorta*); Douglas-fir (*Pseudotsuga menziesii*); the hemlocks which include Western hemlock (*Tsuga heterophylla*), Eastern hemlock (*Tsuga canadensis*), Mountain hemlock (*Tsuga mertensiana*): the spruces which include the Norway spruce (*Picea abies*), Red spruce (*Picea rubens*), White spruce (*Picea glauca*); Black spruce (*Picea mariana*), Sitka spruce (*Picea sitchensis*), Englemann spruce (*Picea engelmanni*), and Blue spruce (*Picea pungens*); redwood (*Sequoia sempervirens*); the true firs including the Alpine fir (*Abies lasiocarpa*), silver fir (*Abies amabilis*), grand fir (*Abies grandis*), noble fir (*Abies procera*), white fir (*Abies concolor*), California red fir (*Abies magnifica*), and balsam fir (*Abies balsamea*); the cedars which include the Western red cedar (*Thuja plicata*), incense cedar (*libocedrus decurrens*), Northern white cedar (*Thuja occidentalis*), Port Orford cedar (*Chamaecyparis lawsoniona*), Atlantic white cedar (*Chamaecyparis thyoides*), Alaska yellow-cedar (*Chamaecyparis nootkatensis*), and Eastern red cedar (*Huniperus virginiana*); the larches which include Eastern larch (*Larix laricina*), Western larch (*Larix occidentalis*), European larch (*Larix decidua*), Japanese larch (*Larix leptolepis*), and Siberian larch (*Larix siberica*); Bold cypress (*Taxodium distichum*); and giant sequoia (*Sequoia gigantea*). The somatic tissue useful in the present invention includes all gymnosperm somatic tissue, not only the somatic tissue of those gymnosperm species specifically enumerated above, although such specifically enumerated gymnosperms can be considered as one preferred class of gymnosperm tissues. Another preferable class is somatic tissue from the pines and spruces. Most preferably, the pine tissue employed is from the loblolly pine (*Pinus taeda*), and the spruce tissue utilized is from the Norway spruce (*Picea abies*).

The somatic tissue employed in the present invention is preferably somatic tissue taken from gymnosperm embryonic tissue, such as that obtained from mature embryos or fertilized ovules. Also useful is somatic tissue taken from the gymnosperm hypocotyl or cotyledon explant.

In accordance with the present invention, the gymnosperm somatic tissue is cultured in a medium containing certain compounds. Specifically, in a first embodiment, somatic tissue is cultured in a medium containing at least about 3% glucose or maltose (*or combinations thereof*) and at least about 10 µM abscisic acid. In a second embodiment of the invention, somatic tissue is cultured first in a medium containing at least about 3% glucose or maltose (*or combinations thereof*) and at least about 10 µM abscisic acid, and then in a medium containing at least about 3% maltose, at least about 20 µM abscisic acid and, optionally but preferably, at least about 0.1 µM indolebutyric acid.

Glucose, one of the compounds employed in the subject invention, is a monosaccharide having a molecular weight of about 180 daltons, and is found in abundant quantities in the plant kingdom. Maltose, another compound employed in the subject invention is also a plant sugar, specifically, a disaccharide having a molecular weight of about 360 daltons. Both sugars are commercially available in purified form Abscisic acid, also employed in the subject invention, is a well known plant hormone which has been found to variously induce stomatal closure, abscision, dormancy, growth inhibition and other responses in plants. Indolebutyric acid, optionally but preferably employed in the invention, is a well known synthetic growth regulator. The latter compound is considered to be a member of the auxin family and has been found, like other auxins, to promote cell growth and division.

As noted above, glucose and/or maltose are variously present in the medium in an amount of at least about 3% by weight based on the total weight of the medium. Preferably, glucose and/or maltose are present in an amount between about 5% and 10%, most preferably about 6%. Generally, the glucose and/or maltose are not present in quantities greater than about 25%

In the first embodiment of the present invention, abscisic acid is present in the medium in an amount of at least about 10 µM, preferably between about 10 µM and 30 µM, most preferably about 20 µM. In the second embodiment, specifically the first step thereof, abscisic acid is present in the medium in an amount of at least about 10 µM, preferably between 10 µM and 30 µM, most preferably about 20 µM. In the second step of the second embodiment of the invention, however, abscisic acid is present in an amount of at least about 20 µM abscisic acid, preferably between about 20 µM and 40 µM, most preferably about 30 µM. Generally, abscisic acid is not present in quantities greater than about 100 µM.

Indolebutyric acid, employed in the second step of the second embodiment of the invention, is present in the medium in an amount of at least about 0.1 µM, preferably between 0.5 µM and 2.0 µM, most preferably 1.0 μM. Generally no more than 10 μM of indolebutyric acid is used.

Within these general parameters, the precise amount of each component to be employed will depend upon various factors, as will be readily apparent to those skilled in the art, such factors including the type of gymnosperm to be cultured. Typically, the compounds are initially employed at the lower levels, and the amounts increased as necessary to achieve the desired effect.

As those skilled in the art would recognize, in addition to producing embryogenesis in accordance with the present invention, the general nutritional and growth requirements of tissue cultured plant cells must be satisfied. The general nutritional and growth requirements of plant cells are well known, and a number of conventional culture media and growth protocols have been developed which satisfy these needs. See, e.g., MSG medium (Becwar, M. R., et al., "Development and Characterization of In Vitro Embryogenic Systems in Conifers", in *Somatic Cell Genetics of Woody Plants*, ed. Ahuja, M. R., Kluwer Academic Publishing, Dordrecht, The Netherlands (*1988*)), Shenk-Hildebrandt (SH) culture medium (Shenk et al., *Can. J. Bot.*, Vol. 50, pp. 199–204 (1972)), Murashige-Skoog (M-S) basal media (Murasige et al., *Physiol. Plant.*, Vol. 15, pp. 473–97 (1962)), and White's medium (White, The Cultivation of Animal and Plant Cells, 2nd ed., Ronald Press Co., New York (1963)). A comprehensive list of plant culture media and culture protocol are found in Huang et al., Plant Tissue Culture Media, TCA Manual, Vol. 3, pp. 539–48, Tissue Culture Association, Rockville, Md. (1977). The disclosures of each of these references are incorporated herein, by reference, in their entirety. The foregoing culture media and culture protocol, as well as others known to those skilled in the art, can be employed in conjunction with the embryogenic methods and medium of the present invention. In accordance with the invention, however, glucose, maltose and abscisic acid must necessarily be present, and indolebutyric acid preferably present, each in the amounts set forth herein, for the efficient and effective production of mature embryonic tissue from the gymnosperm somatic tissue.

As used herein, the term mature refers to embryo development wherein distinct cotyledon primordia are present, overtopped by the shoot apical dome, and wherein shoot apical meristem growth exists, that is, development corresponding to stages IV and V of Buckholz et al., *Ill. Acad. Sci. Transactions*, Vol. 38, pp. 27–50 (1945), the disclosures of which are incorporated herein by reference in their entirety. The mature embryos can then be further employed in various fashions as known to those skilled in the art including use in numerous important research efforts as will be readily apparent to those skilled in the art.

The present invention is further described in the following Examples. These Examples are not to be construed as limiting the appended claims.

EXAMPLE 1

Cones from the loblolly pines (*Pinus taeda*) were obtained. Callus lines were initiated using conventional procedures, such as those described in Becwar, et al., *Can. J. For. Res.* (1990). Calli were maintained in darkness on MSG medium containing 9.0 μM 2,4-dichlorophenoxyacetic acid and 4.0 μM 6-benzylaminopurine using a two week sub-culture regime. Calli were then transferred to BLG basal medium, as described in Verhagen et al., *Plant Cell. Tissue and Organ Cult.*, Vol. 16, pp. 103–111 (1989), with 0.3% activated charcoal, and cultured for a period of one week.

To initiate development and maturation of somatic embroys, the calli were transferred to culture media comprising MSG medium, which was solidified with 0.2% Gelrite ™ (a product available from Merck & Co., Inc.), that had been supplemented with 6% glucose and 20 μM abscisic acid. The calli were subcultured to fresh media every two weeks for a total of about 6 to 8 weeks. Samples of the calli clumps were removed and the number of mature somatic embryos per clump were quantified using the procedures of Becwar et al., *Plant Cell Reports*, Vol. 6, pp. 35–38 (1987). The classification system of Buckolz et al., *Illinois Acad. Sci. Transactions*. Vol. 38, pp. 27–50 (1945) was adopted in categorizing the somatic embryos as mature. Briefly, mature embryos were required to correspond to stages IV and V of Buckholz et al., and, as such, were required to possess distinct cotyledon primordia which were overtopped by the shoot apical dome.

The results of Example 1 are set forth in Table I below.

EXAMPLE 2

The procedures of Example 1 were substantially followed, except that initiation of development and maturation of somatic embryos was carried out as follows.

Specifically, to initiate development and maturation of somatic embryos, the calli were transferred to culture media comprising MSG medium which was solidified with 0.2% Gelrite ™ and supplemented with 6% glucose and 20 μM abscisic acid. The calli were subcultured to fresh media every two weeks for a total of about four weeks. The developing and maturing somatic embryos were then transferred to culture media comprising MSG medium which was solidified with 0.2% Gelrite ™ and supplemented with 6% maltose, 30 μM abscisic acid and 1 μM indolebutyric acid. The emerging embryos were subcultured to fresh media every two weeks for a total of about four to six weeks, at which time samples of the calli clumps were removed and the number of mature somatic embryos per clump were quantified as described in Example 1.

The results of Example 2 are set forth in Table I below.

EXAMPLE 3

The procedures of Example 2 were substantially followed, except that 6% maltose, rather than 6% glucose, was employed in the initiation of development and maturation of the somatic embryos.

The results of Example 3 are set forth in Table I below.

TABLE I

Formation of Mature (Cotyledonary) Somatic Embryos of the Loblolly Pine (*Pinus taeda*).

| Example | Treatment* | No. Mature Embryos per Callus Clump** |
|---|---|---|
| 1 | Culture Medium + 6% Glucose & 20 μM ABA | 0.25 |
| 2 | Culture Medium + 6% Glucose & 20 μM ABA, followed by Culture Medium + 6% Maltose, 30 μM ABA & 1 μM IBA | 1.28 |
| 3 | Culture Medium + 6% Maltose & 20 μM ABA, followed by Culture Medium + | 1.36 |

TABLE I-continued

Formation of Mature (Cotyledonary) Somatic Embryos of the Loblolly Pine (*Pinus taeda*).

| Example | Treatment* | No. Mature Embryos per Callus Clump** |
|---|---|---|
| | 6% Maltose, 30 μM ABA, & 1 μM IBA | |

*ABA = abscisic acid; IBA = indolebutyric acid
**Data represents average number of mature embryos over 4 callus clumps in each of 4 replications in Example 1, and average number of mature embryos over 5 callus clumps in each of 5 replications in Examples 2 and 3.

Although the foregoing invention has been described in some detail by way of illustration for purposes of clarity of understanding, it will be understood that numerous modifications in addition to type described in detail above may be practiced within the spirit and scope of the appended claims.

What is claimed is:

1. A method of producing mature embryonic tissue from embryogenic callus derived from cultured immature zygotic embryos of gymnosperms selected from the group consisting of *Pinus taeda* and *Pseudotsuga menziesii*, said method comprising culturing said callus in a culture medium containing at least about 3% of a sugar selected from the group consisting of glucose and maltose and at least about 10 μM abscisic acid.

2. The method of claim 1 wherein the gymnosperm callus is from *Pinus taeda*.

3. The method of claim 1 wherein the sugar is glucose.

4. The method of claim 1 wherein the sugar is maltose.

5. The method of claim 1 wherein the culture medium contains between about 5% and 10% of the sugar.

6. The method of claim 5 wherein the culture medium contains 6% of the sugar.

7. The method of claim 1 wherein the culture medium contains between about 10 μM and 30 μM abscisic acid.

8. The method of claim 7 wherein the culture medium contains about 20 μM abscisic acid.

9. A method of producing mature embryonic tissue from embryogenic callus derived from cultured immature zygotic embryos of said method comprising culturing said callus in (i) a culture medium containing at least about 3% of a sugar selected from the group consisting of glucose and maltose and at least about 10 μM abscisic acid, and then in (ii) a culture medium containing at least about 3% maltose and at least about 20 μM abscisic acid.

10. The method of claim 9 wherein the culture medium in (ii) further contains at least about 1 μM indolebutyric acid.

11. The method of claim 9 wherein the sugar in (i) is glucose.

12. The method of claim 9 wherein the sugar in (i) is maltose.

13. The method of claim 9 wherein the culture medium in (i) contains between about 5% and 10% of the sugar.

14. The method of claim 13 wherein the culture medium in (i) contains about 6% of the sugar.

15. The method of claim 9 wherein the culture medium in (i) contains between about 10 μM and 30 μM abscisic acid.

16. The method of claim 15 wherein the culture medium in (i) contains about 20 μM abscisic acid.

17. The method of claim 9 wherein the culture medium in (ii) contains between about 20 μM and 40 μM abscisic acid.

18. The method of claim 17 wherein the culture medium in (ii) contains about 30 μM abscisic acid.

19. An embryogenic medium for the production of mature embryonic tissue from embryogenic callus derived from cultured immature zygotic embryos of gymnosperms selected from the group consisting of *Pinus taeda* and *Pseudotsuga menziesii*, wherein said embryogenic medium comprises a culture medium containing at least about 3% of a sugar selected from the group consisting of glucose and maltose and at least about 10 μM abscisic acid.

20. The embryogenic medium of claim 19 wherein the gymnosperm callus is from *Pinus taeda*.

21. The embryogenic medium of claim 19 wherein the sugar is glucose.

22. The embryogenic medium of claim 19 wherein the sugar is maltose.

23. The embryogenic medium of claim 19 wherein the culture medium contains between about 5% and 10% of the sugar.

24. The embryogenic medium of claim 23 wherein the culture medium contains about 6% of the sugar.

25. The embryogenic medium of claim 19 wherein the culture medium contains between about 10 μM and 30 μM abscisic acid.

26. The embryogenic medium of claim 25 wherein the culture medium contains about 20 μM abscisic acid.

27. An embryogenic medium for the production of mature embryonic tissue from embryogenic callus derived from cultured immature zygotic embryos of *Pinus taeda*, wherein said embryogenic medium comprises (i) a culture medium containing at least about 3% of a sugar selected from the group consisting of glucose and maltose and at least about 10 μM abscisic acid, and separately (ii) a culture medium containing at least about 3% maltose and at least about 20 μM abscisic acid.

28. The embryogenic medium of claim 27 wherein the culture medium in (ii) further contains at least about 1 μM indolebutyric acid.

29. The embryogenic medium of claim 27 wherein the sugar in (i) is glucose.

30. The embryogenic medium of claim 27 wherein the sugar in (i) is maltose.

31. The embryogenic medium of claim 27 wherein the culture medium in (i) contains between about 5% and 10% of the sugar.

32. The embryogenic medium claim 31 wherein the culture medium in (i) contains about 6% of the sugar.

33. The embryogenic medium of claim 27 wherein the culture medium in (i) contains between about 10 μM and 30 μM abscisic acid.

34. The embryogenic medium of claim 33 wherein the culture medium in (i) contains about 20 μM abscisic acid.

35. The embryogenic medium of claim 27 wherein the culture medium in (ii) contains between about 20 μM and 40 μM abscisic acid.

36. The embryogenic medium of claim 35 wherein the culture medium in (ii) contains about 30 μM abscisic acid.

37. The method of claim 1 wherein the gymnosperm callus is from *Pseudotsuga menziesii*.

38. The embryogenic medium of claim 19 wherein the gymnosperm callus is from *Pseudotsuga menziesii*.

* * * * *

UNITED STATES PATENT AND TRADEMARK OFFICE
CERTIFICATE OF CORRECTION

PATENT NO. : 5,187,092

DATED : February 16, 1993

INVENTOR(S) : M. Rafique Uddin

It is certified that error appears in the above-identified patent and that said Letters Patent is hereby corrected as shown below:

Column 1, line 31:

"along With" should read "along with".

Column 3, line 28:

"soft woods which" should read "soft woods, which".

Column 3, line 32:

"*(Pinus elliotti)*, should read "*(Pinus elliotii)*,".

Column 3, line 33:

"*(Pinus palustrus)*," should read "*(Pinus palustris)*,".

Column 3, line 59:

"*(Huniperus*" should read "*(Juniperus*".

Column 7, line 45, Claim 9:

UNITED STATES PATENT AND TRADEMARK OFFICE
CERTIFICATE OF CORRECTION

PATENT NO. : 5,187,092

DATED : February 16, 1993

INVENTOR(S) : M. Rafique Uddin

It is certified that error appears in the above-identified patent and that said Letters Patent is hereby corrected as shown below:

Column 7, line 45, Claim 9:

"embryos of said method" should read "embryos of Pinus taeda, said method".

Signed and Sealed this

Twenty-third Day of November, 1993

*Attest:*

BRUCE LEHMAN

*Attesting Officer*     *Commissioner of Patents and Trademarks*